(12) United States Patent
Hamman (10) Patent No.: US 8,657,212 B2
(45) Date of Patent: Feb. 25, 2014

(54) MULTI-FLUID BLENDING SPRAY TIP FOR COAXIAL SYRINGE

(75) Inventor: Ned M. Hamman, Leesburg, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 237 days.

(21) Appl. No.: 13/193,820

(22) Filed: Jul. 29, 2011

(65) Prior Publication Data

US 2013/0026255 A1    Jan. 31, 2013

(51) Int. Cl.
*B05B 7/10*      (2006.01)

(52) U.S. Cl.
USPC ............................................ 239/403; 239/399

(58) Field of Classification Search
USPC ................. 239/398, 399, 406, 421, 423, 424; 606/41, 42, 45–50
See application file for complete search history.

(56) References Cited

U.S. PATENT DOCUMENTS

| | | | |
|---|---|---|---|
| 2,890,836 A | | 6/1959 | Gusmer et al. |
| 4,923,448 A | | 5/1990 | Ennis, III |
| 5,246,014 A | * | 9/1993 | Williams et al. ............. 607/122 |
| 5,368,563 A | | 11/1994 | Lonneman et al. |
| 5,431,649 A | * | 7/1995 | Mulier et al. .................... 606/41 |
| 5,458,597 A | * | 10/1995 | Edwards et al. ................ 606/41 |
| 5,807,395 A | * | 9/1998 | Mulier et al. ................... 606/41 |
| 5,814,022 A | | 9/1998 | Antanavich et al. |
| 6,328,229 B1 | | 12/2001 | Duronio et al. |
| 7,232,080 B2 | | 6/2007 | Kutay et al. |

FOREIGN PATENT DOCUMENTS

| | | |
|---|---|---|
| WO | WO-0037178 A1 | 6/2000 |
| WO | WO-2009050449 A1 | 4/2009 |
| WO | WO-2013019606 A1 | 2/2013 |

OTHER PUBLICATIONS

International Search Report and Written Opinion mailed Dec. 6, 2012 for PCT/US2012/048512 which claims benefit of U.S. Appl. No. 13/193,820, filed Jul. 9, 2011.

* cited by examiner

*Primary Examiner* — Davis Hwu
(74) *Attorney, Agent, or Firm* — Harness, Dickey (57) ABSTRACT

A coaxial syringe spray assembly that includes a first receptacle defined by the assembly, a second receptacle defined by the assembly and in coaxial alignment with the first receptacle, and a spray tip assembly configured to be in fluid communication with both the first receptacle and the second receptacle. The spray tip defines a first fluid chamber in fluid communication with the first receptacle, a second fluid chamber in fluid communication with the first receptacle, and an outlet port that defines a blending chamber that is in fluid communication with the second receptacle, the first fluid chamber, and the second fluid chamber such that a first fluid introduced into the first fluid chamber and a second fluid introduced into the second fluid chamber are mixed in the blending chamber to provide a mixture having a helical flow pattern.

20 Claims, 11 Drawing Sheets

MULTI-FLUID BLENDING SPRAY TIP FOR COAXIAL SYRINGE

FIELD

The present disclosure relates to a multi-fluid blending spray tip for a coaxial syringe.

BACKGROUND

This section provides background information related to the present disclosure which is not necessarily prior art.

Various medical procedures include mixing two or more components together and delivering the mixture to a particular location. For example, to facilitate wound healing a mixture of blood and clotting serum can be delivered to a wound site. While devices and methods exist for mixing biological components prior to delivery, they are subject to improvement.

SUMMARY

This section provides a general summary of the disclosure, and is not a comprehensive disclosure of its full scope or all of its features.

The present teachings provide for a coaxial syringe spray assembly that includes a first receptacle defined by the assembly, a second receptacle defined by the assembly and in coaxial alignment with the first receptacle, and a spray tip assembly configured to be in fluid communication with both the first receptacle and the second receptacle. The spray tip defines a first fluid chamber in fluid communication with the first receptacle, a second fluid chamber in fluid communication with the first receptacle, and an outlet port that defines a blending chamber that is in fluid communication with the second receptacle, the first fluid chamber, and the second fluid chamber such that a first fluid introduced into the first fluid chamber and a second fluid introduced into the second fluid chamber are mixed in the blending chamber to provide a mixture having a helical flow pattern.

The present teachings further provide for a coaxial syringe spray assembly including a first receptacle, a second receptacle, and a spray tip assembly. The first receptacle is defined by the assembly and configured to contain a first fluid. The second receptacle is defined by the assembly, is in coaxial alignment with the first receptacle, and is configured to contain a second fluid. The spray tip assembly is configured to be in fluid communication with the first receptacle and the second receptacle. The spray tip assembly defines a blending chamber, a first fluid chamber, a second fluid chamber, and an outlet port. The blending chamber is in fluid communication with both the first receptacle and the second receptacle. The first fluid chamber is in fluid communication with the first receptacle and connected to a first portion of the blending chamber. The second fluid chamber is in fluid communication with the first receptacle and connected to a second portion of the blending chamber that is opposite to the first portion of the blending chamber such that the first fluid entering the blending chamber from the first fluid chamber travels in a direction opposite to the first fluid entering the blending chamber from the second fluid chamber. The first and the second fluids are mixed in the blending chamber to provide a mixture having a helical flow pattern. The outlet port that defines the blending chamber, the outlet port includes an outlet for the mixture to exit the spray tip.

The present teachings also provide for a coaxial syringe spray assembly configured to mix blood and clotting serum. The assembly includes a first receptacle, a second receptacle, and a spray tip assembly. The first receptacle is defined by the assembly and configured to contain the blood therein. The second receptacle is defined by the assembly, is in coaxial alignment with the first receptacle, and surrounded by the first receptacle. The second receptacle is configured to contain the clotting serum therein. The spray tip assembly is configured to be in fluid communication with the first receptacle and the second receptacle. The spray tip assembly includes a blending chamber, a first conduit, a second conduit, a third conduit, and an outlet port. The first conduit is configured to convey the clotting serum from the second receptacle to the blending chamber. The first conduit is partially defined by a boss that extends within the blending chamber. The second conduit is configured to convey the blood from the first receptacle to a first portion of the blending chamber. The third conduit is configured to convey the blood from the first receptacle to a second portion of the blending chamber that is opposite to the first portion such that blood from the first conduit and blood from the second conduit flow into the blending chamber in opposite directions. The blood flows around an exterior of the boss. The clotting serum and the blood are mixed in the blending chamber to provide a clotting mixture having a helical flow pattern upon exiting the spray tip at the outlet port.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

With initial reference to FIGS. 1-4, a coaxial syringe spray assembly is generally illustrated at reference numeral 10. The spray assembly 10 generally includes an outer body 12, an outer plunger 14, an inner plunger 16, a center tube 18 between the outer plunger 14 and the inner plunger 16, a body adaptor 20 for supporting the center tube 18 and a spray tip assembly 22 configured to be removably mounted to the body adaptor 20.

The outer body 12 includes a first outer body end 24 and a second outer body end 26 that is opposite to the first outer body end 24. Extending between the first outer body end 24 and the second outer body end 26 is an outer sidewall 28 and an inner sidewall 30, which is opposite to the outer sidewall 28. The inner sidewall 30 is generally cylindrical and defines a housing 32, which is open at the first and the second outer body ends 24 and 26. A longitudinal axis A (FIG. 3, for example) extends through an axial center of the housing 32 from the first outer body end 24 to the second outer body end 26. A first handle 34 and a second handle 36 extend from opposite sides of the outer sidewall 28. The first handle 34 and the second handle 36 are each illustrated as a looped structure that defines a space suitable to accommodate a typical finger to facilitate operation of the coaxial syringe spray assembly 10.

Figures 1, 3:
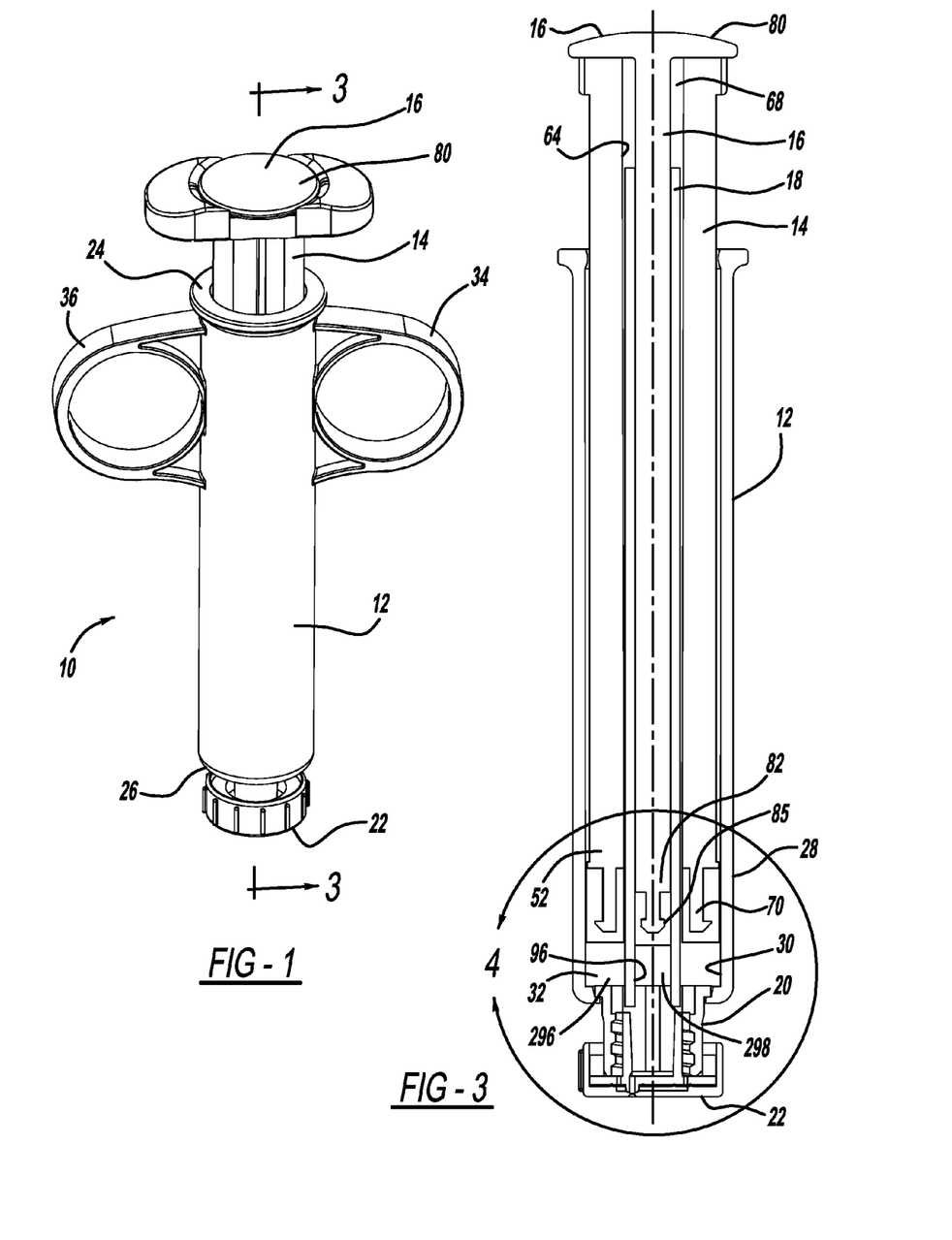
FIG. 1 is a perspective view of a coaxial syringe spray assembly according to the present teachings.
FIG. 3 is a cross-sectional view of the coaxial syringe spray assembly of FIG. 1 taken along line 3-3 of FIG. 1.

The outer plunger 14 generally includes an outer plunger head 50, an outer plunger tip 52, and an outer plunger shaft 54 that extends between the outer plunger head 50 and the outer plunger tip 52. The outer plunger head 50 includes a first lever 56 that is opposite to a second lever 58. The outer plunger head 50 defines an outer plunger head recess 60 between the first lever 56 and the second lever 58. The outer plunger shaft 54 includes an outer surface 62 and an inner surface 64, which is opposite to the outer surface 62. Extending from the outer surface 62 are four evenly spaced alignment fins 66. The inner surface 64 defines a plunger bore 68, which extends from the outer plunger head 50 to the outer plunger tip 52. As illustrated in FIG. 3 for example, the outer plunger tip 52 includes outer locking tabs 70, which are configured to cooperate with and secure thereto an outer compliant cover 72. The outer complaint cover 72 includes an outer diameter that is proximate to an inner diameter of the housing 32 such that the outer compliant cover 72 contacts the inner sidewall 30 when the outer plunger shaft 54 is seated within the housing 32. The outer compliant cover 72 can be made of any suitable material, such as rubber.

The inner plunger 16 includes an inner head 80, an inner plunger tip 82, and an inner plunger shaft 84 that extends between the inner head 80 and the inner plunger tip 82. The inner head 80 is generally disk-shaped and can be solid. The inner plunger tip 82 includes an inner locking tab 85 (FIG. 3) to which an inner compliant cover 86 is mounted to. The inner compliant cover 86 can be made of any suitable material, such as rubber. The inner plunger shaft 84 is generally solid.

The center tube 18 generally includes a first tube end 90 and a second tube end 92 that is opposite to the first tube end 90. An outer tube surface 94 and an inner tube surface 96 each extend between the first tube end 90 and the second tube end 92. The outer tube surface 94 is opposite to the inner tube surface 96. The inner tube surface 96 is cylindrical and defines a tube bore 98, which is open at the first tube end 90 and the second tube end 92.

Figures 5, 6:
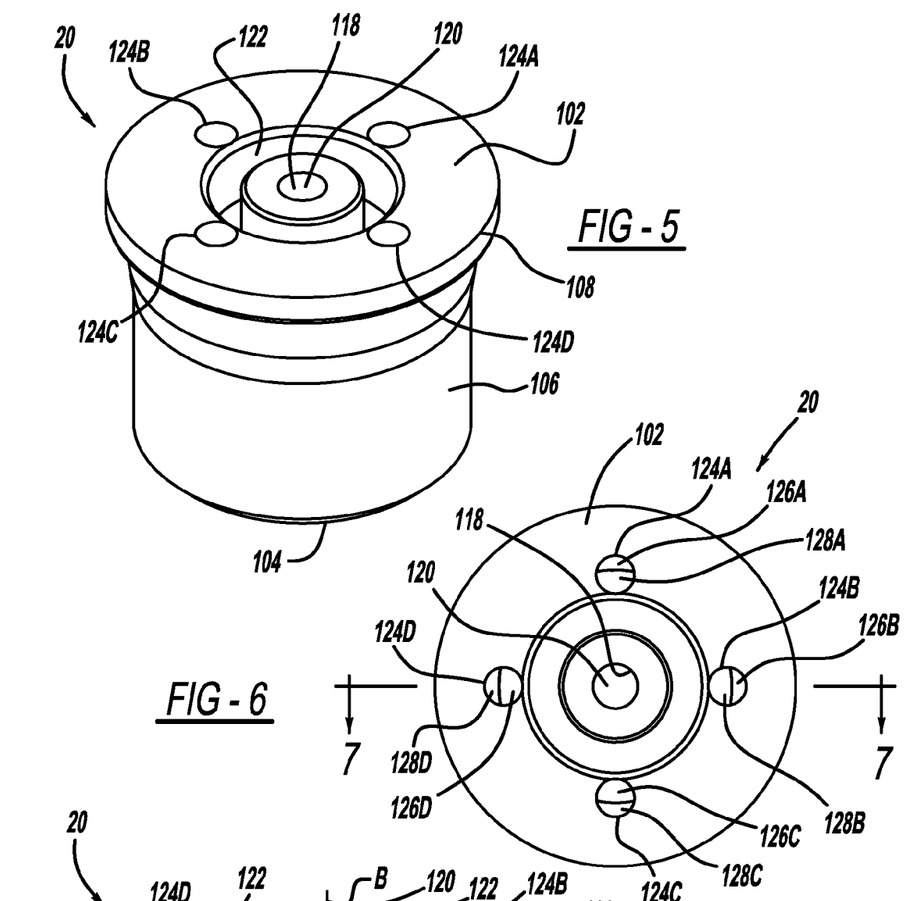
FIG. 5 is a perspective view of a body adaptor of the coaxial syringe spray assembly of FIG. 1.
FIG. 6 is a top view of the body adaptor.
Figure 7:
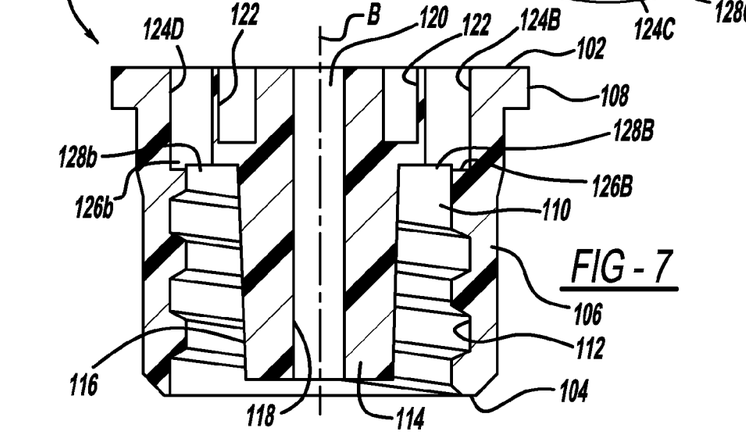
FIG. 7 is a cross-sectional view of the body adaptor taken along line 7-7 of FIG. 6.

With additional reference to FIGS. 5-7, the body adaptor 20 includes a first end 102, a second end 104 that is opposite to the first end 102, and an outer wall 106 that extends between the first end 102 and the second end 104. The outer wall 106 generally includes an adaptor flange 108 at the first end 102. Opposite to the outer wall 106 is an inner wall 110 (FIG. 7), which defines a plurality of internal threads 112 therein. At a center of the body adaptor 20 aligned along a longitudinal axis B thereof (FIG. 7), is a male luer lock fitting 114, which includes a tapered outer surface 116 and an inner surface 118. The inner surface 118 surrounds the longitudinal axis B and defines a center bore 120, which extends along the longitudinal axis B. The center bore 120 extends from the first end 102 to the second end 104, and is open at each of the first end 102 and the second end 104. At the first end 102 is an annular recess 122, which surrounds the center bore 120 and is centered about the longitudinal axis B.

The body adaptor 20 also defines four body apertures 124A-D, which are evenly spaced apart about the longitudinal axis B and positioned such that the annular recess 122 is between the longitudinal axis B and the body apertures 124A-D. The body apertures 124A-D are recessed within, and partially defined by, the first end 102. The body apertures 124A-D each include a base surface 126A-D, which defines an opening 128A-D in each of the body apertures 124A-D. The body apertures 124A-D thus define a passageway from the first end 102 to an area of the body adaptor 20 between the inner wall 110 and the male luer lock fitting 114.

Figures 8, 9, 10:
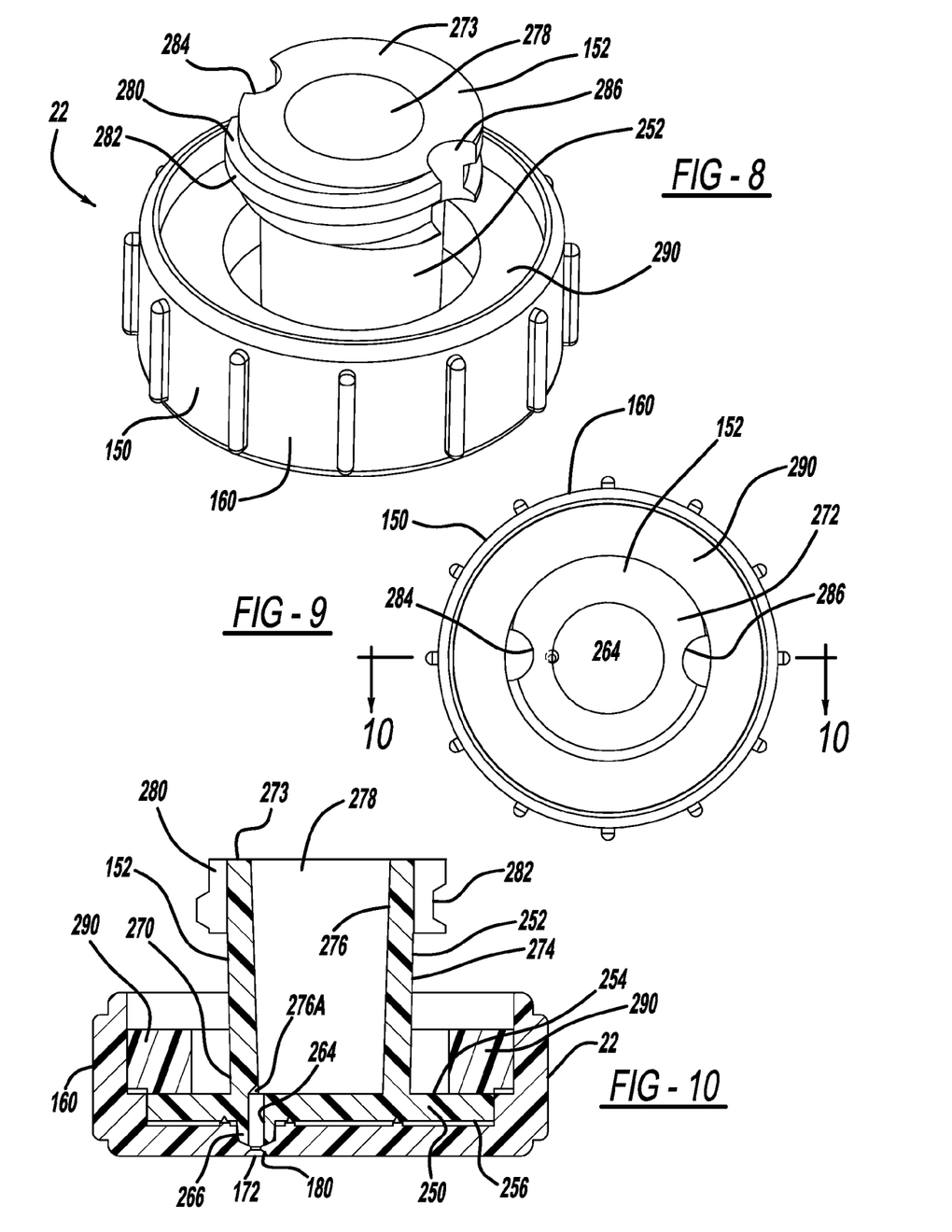
FIG. 8 is a perspective view of a spray tip assembly of the coaxial syringe spray assembly of FIG. 1.
FIG. 9 is a top view of the spray tip assembly of FIG. 8.
FIG. 10 is a cross-sectional view of the spray tip assembly taken along line 10-10 of FIG. 9.

With additional reference to FIGS. 8-10, the spray tip assembly 22 generally includes a spray tip housing 150 and a spray tip insert 152. With yet additional reference to FIGS. 11-16, the spray tip housing 150 includes a housing base 154 having a first surface 156 and a second surface 158 that is opposite to the first surface 156. Both the first surface 156 and the second surface 158 are planar.

Extending from an outer periphery of the housing base 154 and from the first surface 156 is a cylindrical sidewall 160 having an inner sidewall surface 162 and an outer sidewall surface 164. The outer sidewall surface 164 includes a plurality of ridges 166 extending about an outer periphery of the outer sidewall surface 164. Extending from the inner sidewall surface 162 at the first surface 156 of the housing base 154 is a first locator tab 168 and a second locator tab 170. The first locator tab 168 is opposite to the second locator tab 170. The first locator tab 168 extends along a smaller portion of the inner sidewall surface 162 than the second locator tab 170 does.

Figure 16:
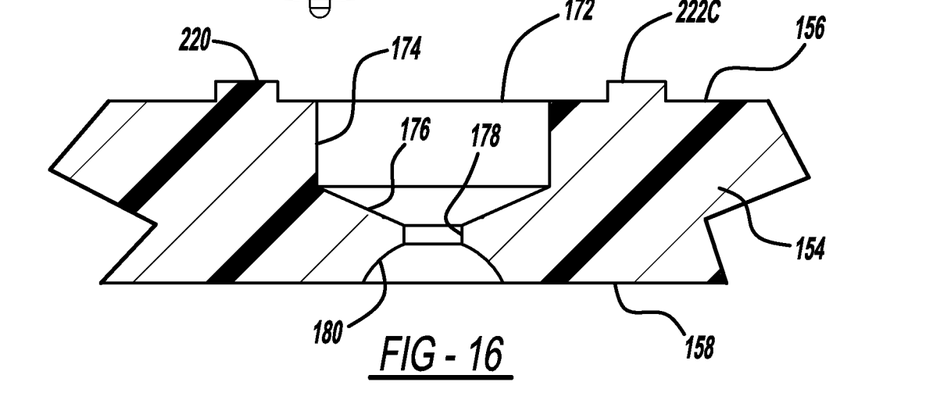
FIG. 16 illustrates the detail at area 16 of FIG. 13.

The housing base 154 defines an outlet port 172 that extends through the housing base 154 from the first surface 156 to the second surface 158. As further described herein, the outlet port 172 is generally a blending chamber. With particular reference to FIG. 16, the outlet port 172 includes a first cylindrical diameter portion 174 proximate to the first surface 156, a tapered portion 176 that extends from the first cylindrical diameter portion 174 to a second cylindrical diameter portion 178, and a conical portion 180 that extends from the second cylindrical diameter portion 178 to the second surface 158. The second cylindrical diameter portion 178 has the smallest diameter of the outlet port 172. The small diameter of the second cylindrical diameter portion 178 concentrates an output as it passes through the outlet port 172 to increase pressure of the output. The conical portion 180 has a greater diameter than the second diameter portion 178 and helps to shape the output into a mist or spray as its exits the outlet port 172, as further described herein. The outlet port 172 is offset from an axial center of the housing base 154 and is between the first locator tab 168 and the second locator tab 170, but may be arranged at any other suitable position of the housing base 154.

Figures 11, 12, 13:
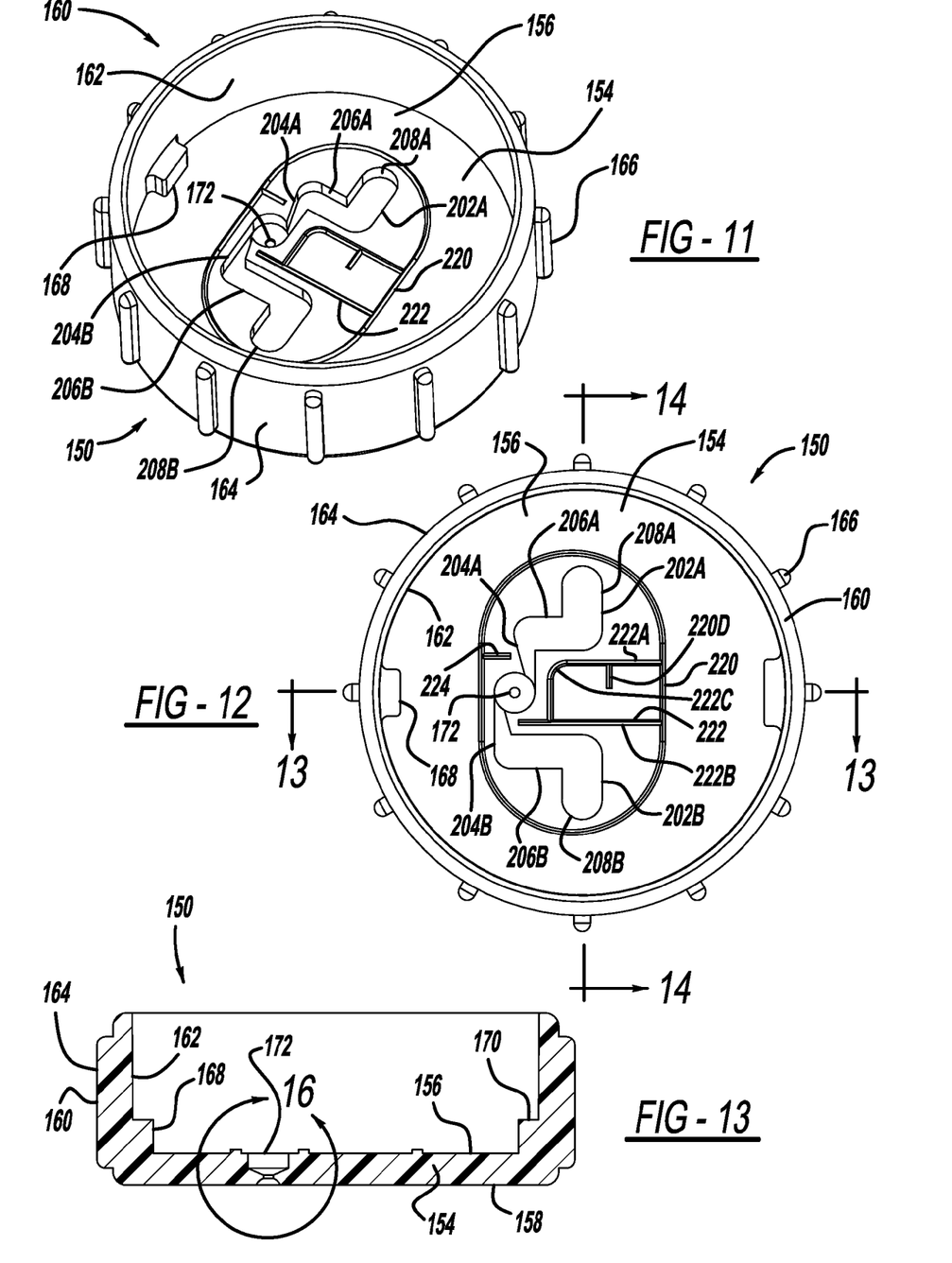
FIG. 11 is a perspective view of a spray tip housing of the spray tip assembly of FIG. 8.
FIG. 12 is a top view of the spray tip housing.
FIG. 13 is a cross-sectional view of the spray tip housing taken along line 13-13 of FIG. 12.
Figure 14:
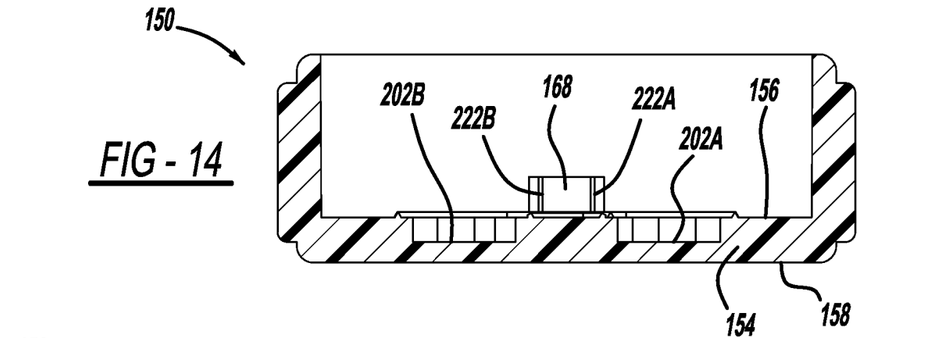
FIG. 14 is a cross-sectional view of the spray tip housing taken along line 14-14 of FIG. 12.
Figure 15:
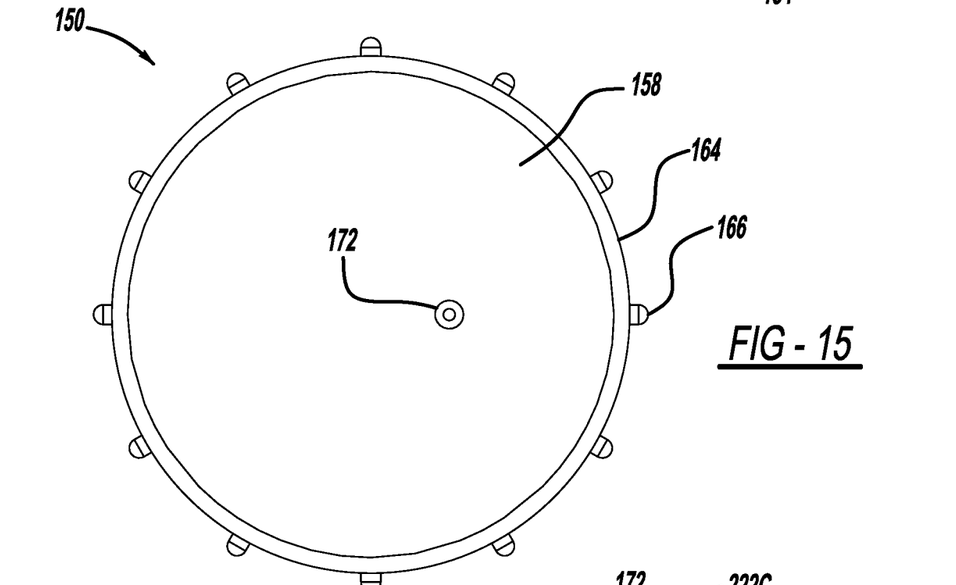
FIG. 15 is a bottom view of the spray tip housing.

The housing base 154 further defines recessed, in the first surface 156, a first fluid chamber 202A and a second fluid chamber 202B. The first fluid chamber 202A generally includes a first portion 204A, a second portion 206A, and a third portion 208A. The second fluid chamber 202B generally includes a first portion 204B, a second portion 206B, and a third portion 208B. The first fluid chamber 202A and the second fluid chamber 202B are on opposite sides of the outlet port 172.

The first portion 204A and the first portion 204B extend from opposite sides of the outlet port 172, with the first portion 204A nearest the second locator tab 170 and the first portion 204B nearest the first locator tab 168. Each of the first portion 204A and the first portion 204B are most narrow at the outlet port 172, and gradually increase in width as they extend away from the outlet port 172. The second portion 206A extends from the first portion 204A and is orientated at about 90° relative to the first portion 204A. Similarly, the second portion 206B extends from the first portion 204B at about 90° relative to the first portion 204B. The second portion 206A is substantially similar to the second portion 206B. The third portion 208A extends from the second portion 206A at about 90° relative to the second portion 206A. Similarly, the third portion 208B extends from the second portion 206B at about 90° relative to the second portion 206B. The third portion 208A and the third portion 208B extend in opposite directions and are substantially similar.

The housing base 154 further includes a generally oval protrusion 220, which extends from the housing base 154 and surrounds the first fluid chamber 202A, the second fluid chamber 202B, and the outlet port 172. The oval protrusion 220 is generally a weld surface for welding the spray tip housing 150 to the spray tip insert 152, such as by ultrasonic welding, as further described herein.

Extending inward from a portion of the oval protrusion 220 nearest the second locator tab 170 is an inner protrusion 222 positioned between the first fluid chamber 202A and the second fluid chamber 202B. The inner protrusion 222 can be of any suitable shape or design. As illustrated, the inner protrusion 222 includes a first linear portion 222A and a second linear portion 222B, which is parallel to the first linear portion 222A. The second linear portion 222B extends further inward from the oval protrusion 220 than the first linear portion 222A. A connecting portion 222C, which includes a curved portion, connects the first linear portion 222A to the second linear portion 222B. Extending from the first linear portion 222A toward the second linear portion 222B is a first tabbed portion 222D. Extending inward from a portion of the oval protrusion 220 nearest the first locator tab 168 and opposite to the inner protrusion 222, is a second tabbed portion 224.

With additional reference to FIGS. 17-21, the spray tip insert 152 will now be described. The spray tip insert 152 generally includes an insert base 250 and an insert stem 252. The insert base 250 includes a first surface 254 and a second surface 256, which is opposite to the first surface 254. The insert stem 252 extends from the first surface 254. The insert base 250 is generally circular and includes at its outer periphery a first notch 258 and a second notch 260, which is opposite to the first notch 258. The first notch 258 extends across a smaller portion of the outer periphery of the insert base 250 than the second notch 260 does, and in this manner the first notch 258 is smaller than the second notch 260. The first notch 258 is generally sized and shaped to receive the first locator tab 168 and the second notch 260 is generally sized and shaped to receive the second locator tab 170.

Figures 17, 18, 19:
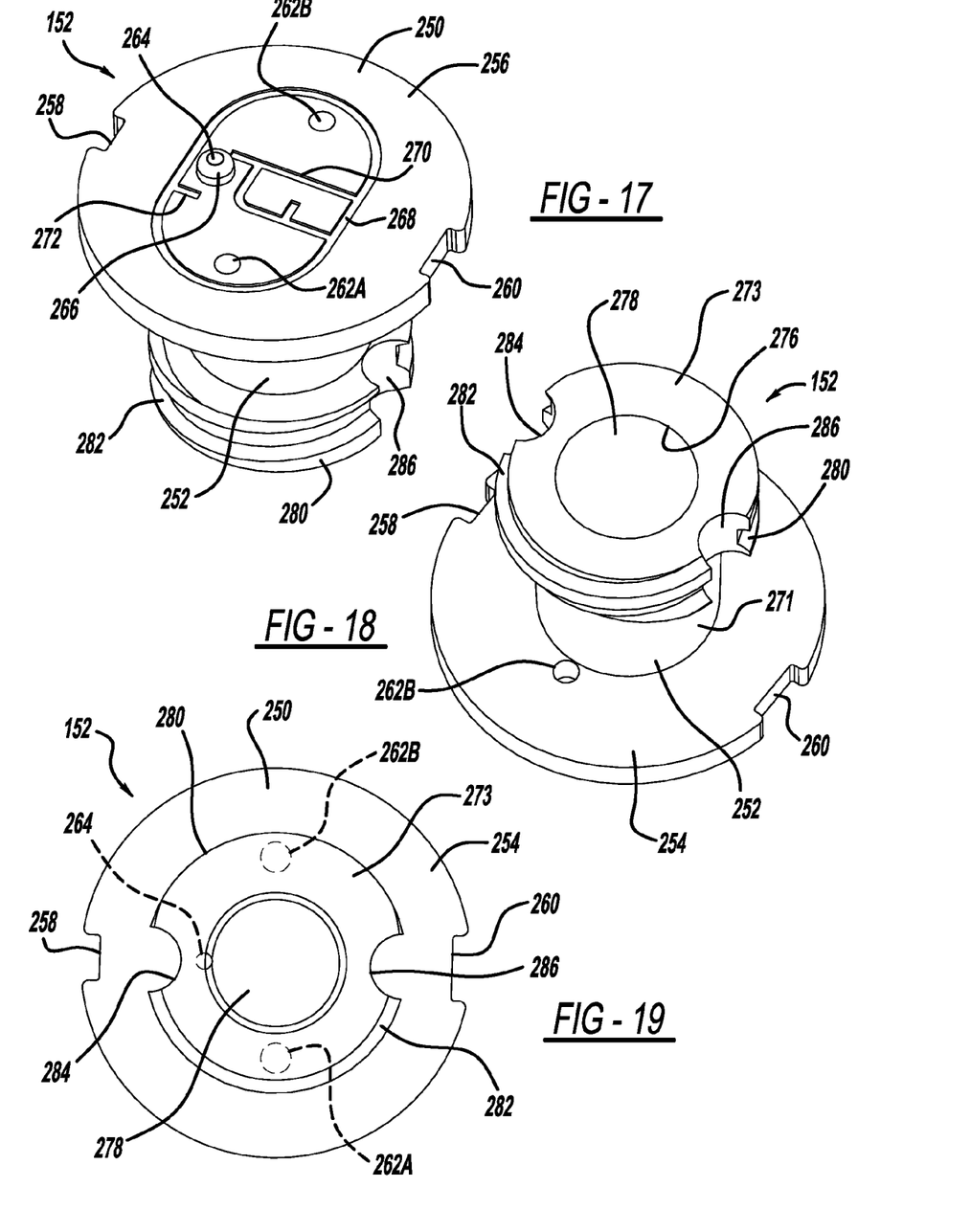
FIG. 17 is a perspective view of a spray tip insert of the spray tip assembly of FIG. 8.
FIG. 18 is another perspective view of the spray tip insert.
FIG. 19 is a top view of the spray tip insert.
Figure 20:
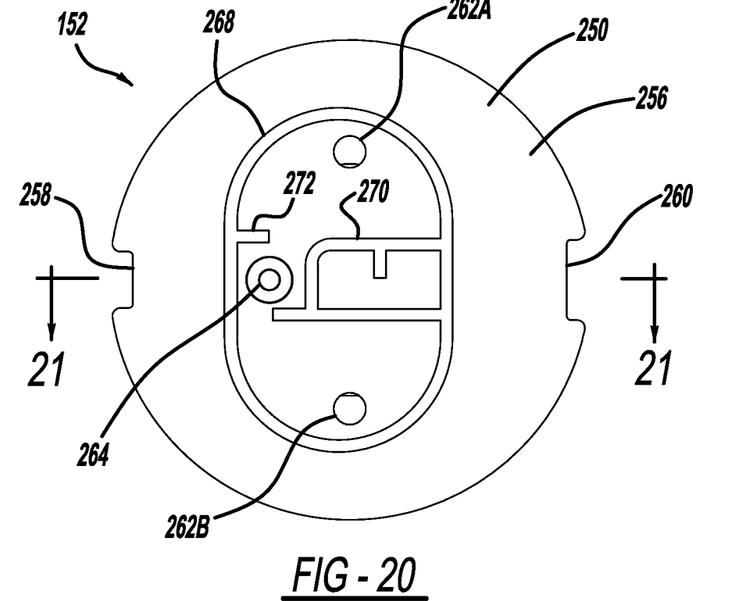
FIG. 20 is a bottom view of the spray tip insert.

The insert base 250 defines a first outer aperture 262A, a second outer aperture 262B, and a center aperture 264 generally between the first outer aperture 262A and the second outer aperture 262B, but offset from an axial center of the insert base 250. The first and second outer apertures 262A and 262B are generally aligned with each other across the insert base 250 half way between the first notch 258 and the second notch 260. The center aperture 264 is about half way between the first outer aperture 262A and the second outer aperture 262B and aligned between the first notch 258 and the second notch 260. The center aperture 264 is closer to the first notch 258 and thus is offset from a line extending between the first outer aperture 262A and the second outer aperture 262B. Each of the first outer aperture 262A, the second outer aperture 262B, and the center aperture 264 extend between the first surface 254 and the second surface 256.

Further defining the center aperture 264 at the second surface 256 of the insert base 250 is a boss 266. The boss 266 is sized and shaped to be received within the first cylindrical diameter portion 174 of the outlet port 172 of the housing base 154.

Recessed within the second surface 256 of the insert base 250 is an oval recess 268, which surrounds the first and second outer apertures 262A, 262B, as well as the center aperture 264. The oval recess 268 is sized and shaped to cooperate with the oval protrusion 220. Extending inward from the oval recess 268 is an inner recess 270, which is sized and shaped to receive the inner protrusion 222, and an inner tab 272, which is sized and shaped to receive the second tabbed portion 224.

Figure 2:
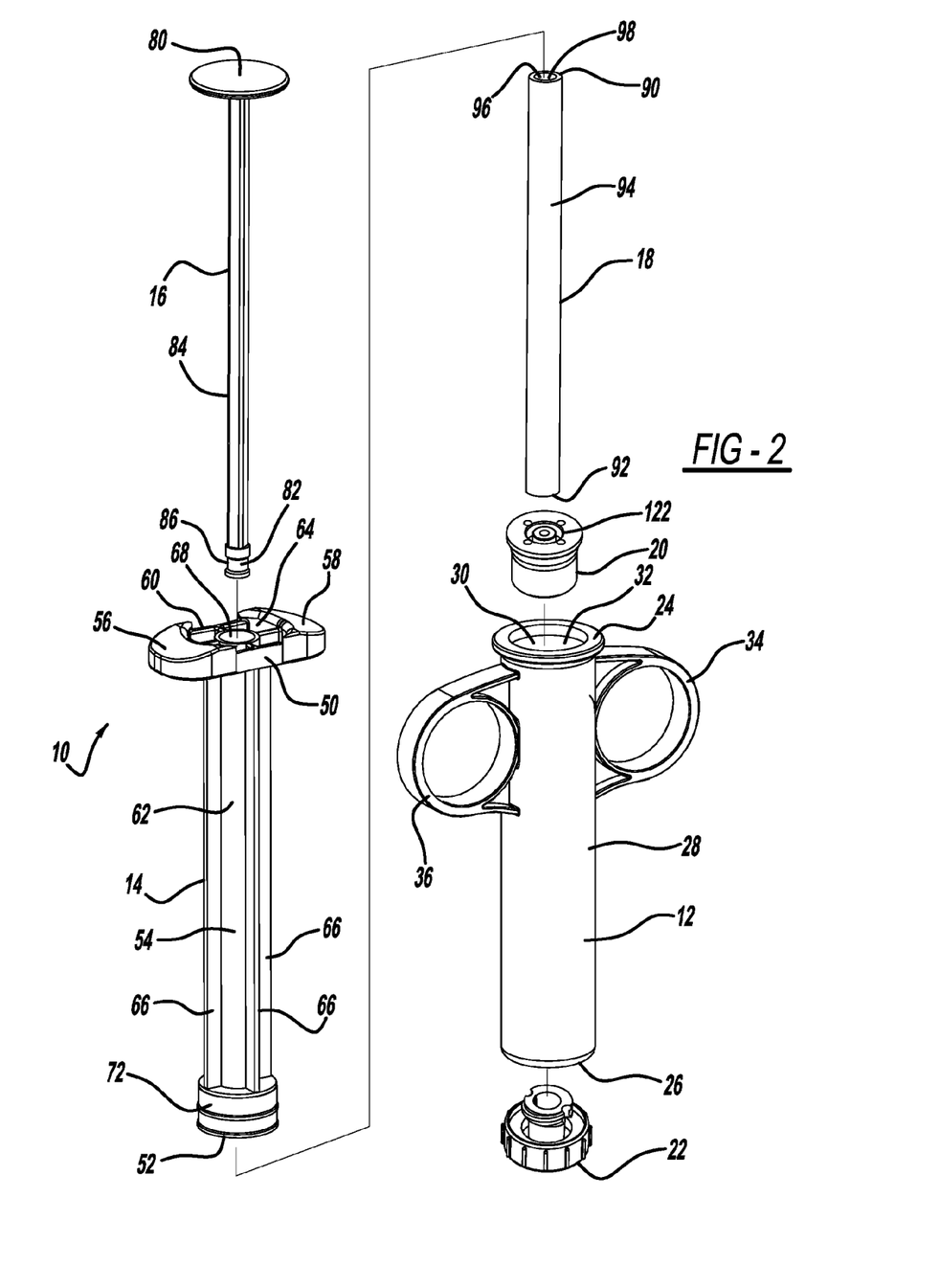
FIG. 2 is an exploded view of the coaxial syringe spray assembly of FIG. 1.

The insert stem 252 extends from the first surface 254 of the insert base 250 and the insert stem 252 is generally centered about an axial center of the insert base 250. The insert stem 252 generally includes a proximal end 271 at the first surface 254 and a distal end 273 opposite to the proximal end 271. Extending between the proximal end 271 and the distal end 273 is an outer sidewall 274 and an inner sidewall 276, which is opposite to the outer sidewall 274 (FIG. 2). The inner sidewall 276 is generally cylindrical and defines an insert receptacle 278, which is open at the distal end 273. Both the outer sidewall 274 and the inner sidewall 276 are tapered inward. The inner sidewall 276 and the insert receptacle 278 thus generally provide a female luer lock. At the distal end 273 is a stem flange 280, which defines a plurality of threads 282. The stem flange 280 defines a first recess 284 and a second recess 286 that is opposite to the first recess 284. The first recess 284 is generally aligned with the first notch 258 of the insert base 250 and the second recess 286 is generally aligned with the second notch 260 of the insert base 250.

Figure 21:
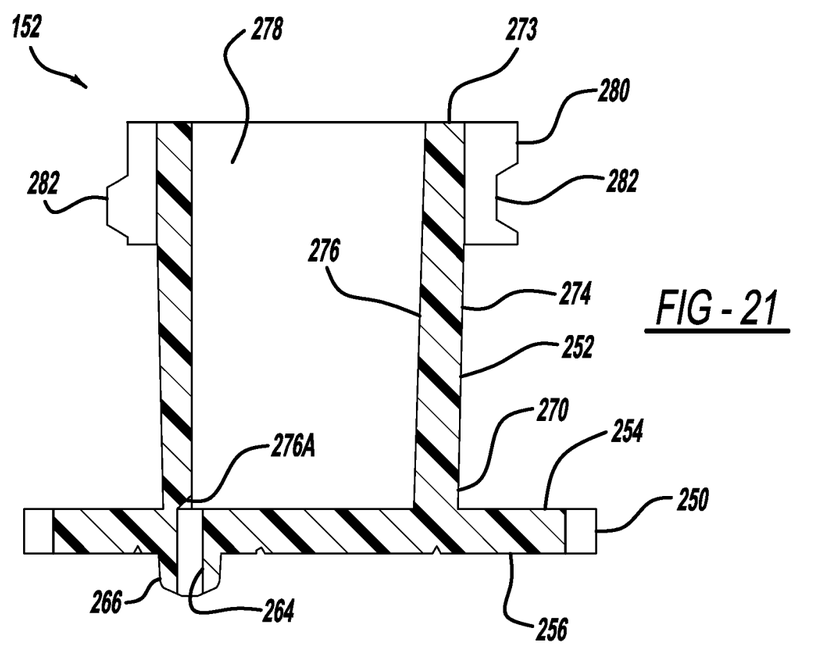
FIG. 21 is a cross-sectional view taken along line 21-21 of FIG. 20.

With reference to FIG. 21 for example, the inner sidewall 276 includes a recessed portion 276A at the center aperture 264. The recessed portion 276A facilitates flow of material out from within the insert receptacle 278 through the center aperture 264. The remainder of the inner sidewall 276 above and proximate to the center aperture 264 extends across about half of the center aperture 264.

Figure 22:
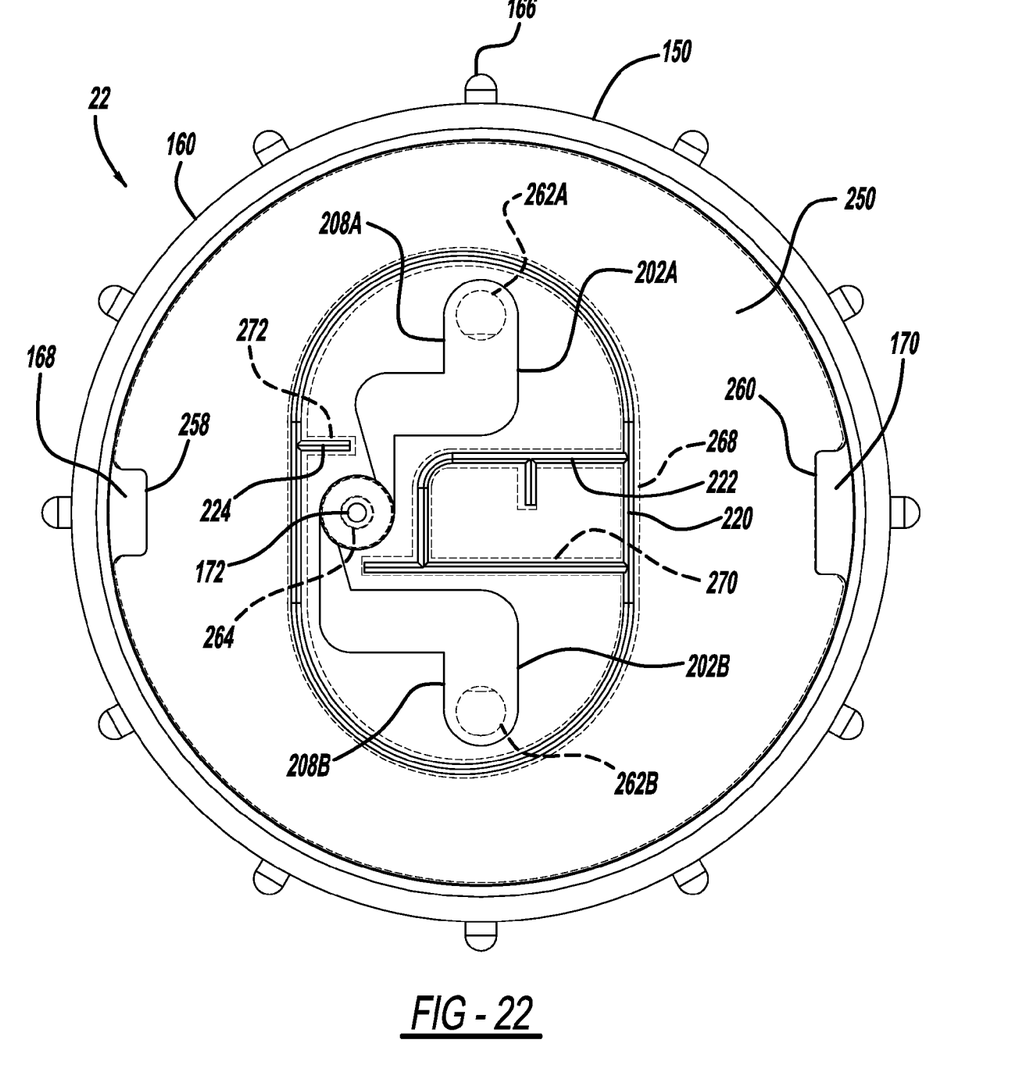
FIG. 22 is a top view of the spray tip housing with detail of the spray tip insert overlaid thereon.

With continued reference to FIGS. 8-10 and additional reference to FIG. 22 for example, assembly of the spray tip assembly 22 will now be described. The insert base 250 is seated within the cylindrical sidewall 160 of the spray tip housing 150 such that the second surface 256 of the insert base 250 is seated on the housing base 154 of the spray tip housing 150. As illustrated in FIG. 22, the insert base 250 is orientated such that the first notch 258 and the second notch 260 of the insert base 250 receive the first locator tab 168 and the second locator tab 170 respectively. The boss 266 of the insert base 250 is seated within the outlet port 172 of the spray tip housing 150. The first outer aperture 262A of the insert base 250 is aligned with the third portion 208A of the first fluid chamber 202A of the spray tip housing 150. The second outer aperture 262B of the insert base 250 is aligned with the third portion 208B of the second fluid chamber 202B of the tip spray housing 150. The generally oval protrusion 220, the inner protrusion 222, and the second tabbed portion 224 of the spray tip housing 150 are each received in the oval recess 268, the inner recess 270, and the inner tab 272 of the insert base 250 respectively. The inert base 250 is then fastened to the spray tip housing 150 in any suitable manner, such as through ultrasonic welding.

Figure 4:
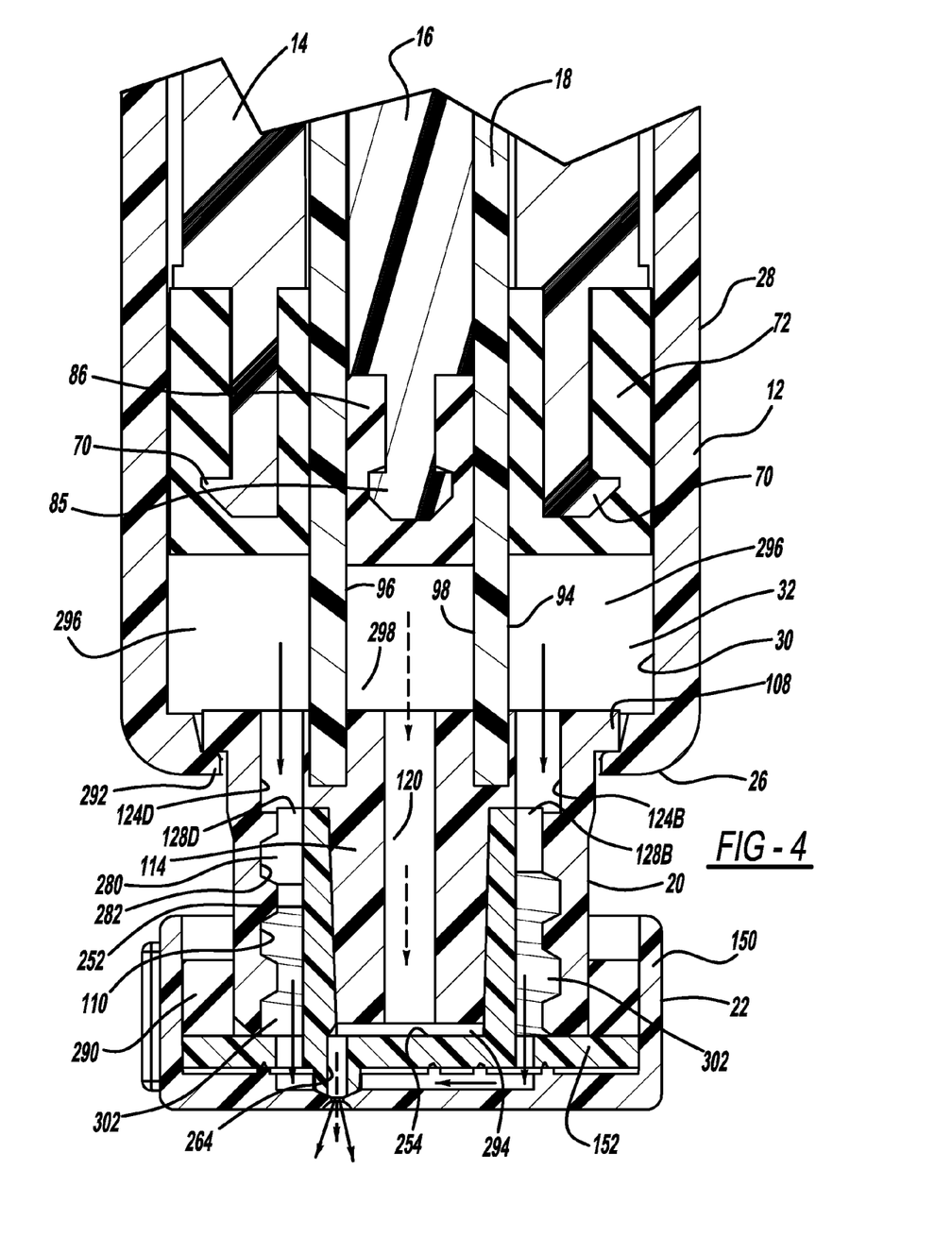
FIG. 4 illustrates the detail at area 4 of FIG. 3.

With reference to FIGS. 4 and 10 for example, the spray tip assembly 22 can further include a washer 290 seated on the first surface 254 of the spray tip insert 152 and along an inner sidewall surface 162 of the spray tip housing 150. The washer 290 is spaced apart from the insert stem 252. The washer 290 can be any suitable washer, such as a polymeric ring washer. The washer 290 contributes to providing a seal between the spray tip assembly 22 and the body adaptor 20.

With reference to FIGS. 1-4 and 22, for example, assembly of the remainder of the coaxial syringe spray assembly 10 will be described. The center tube 18 is mated with the body adaptor 20 by inserting the second tube end 92 into the annular recess 122 of the body adaptor 20. The second tube end 92 can be secured to the body adaptor 20 in any suitable manner, such as with an adhesive. With the center tube 18 secured thereto, the body adaptor 20 is inserted into the housing 32 of the outer body 12 through the first outer body end 24. As illustrated in FIG. 4 for example, the adaptor flange 108 of the body adaptor 20 is seated at the second outer body end 26 on a ledge 292 at the second outer body end 26. Thus, a majority of the body adaptor 20 extends out from within the outer body 12. The body adaptor 20 is secured at the second outer body end 26 in any suitable manner, such as with an ultrasonic weld.

The outer plunger 14 is inserted into the outer body 12 over the center tube 18 such that the center tube 18 is seated within the plunger bore 68. Prior to being inserted within the outer body 12, a syringe lubricant can be applied to the outer plunger 14 to assist movement of the outer plunger 14 along the longitudinal axis A of the coaxial syringe spray assembly 10. Next, the inner plunger 16 is inserted into the tube bore 98 of the center tube 18, and thus the inner plunger shaft 84 is also within the plunger bore 68 of the outer plunger 14. The inner head 80 of the inner plunger 16 is seated within the outer head recess 60 of the outer plunger 14 and secured therein, such as with a suitable adhesive. Prior to being inserted within the center tube 18, a suitable syringe lubricant can be applied to the inner plunger 16 to facilitate movement of the inner plunger 16 within the center tube 18 along the longitudinal axis A. Because the inner plunger 16 and the outer plunger 14 are secured together, they move in tandem along the longitudinal axis A.

As illustrated in FIG. 4 for example, the housing 32 is generally divided into an outer receptacle or chamber 296 and an inner receptacle or chamber 298, which is in coaxial alignment with the outer receptacle 296. The outer receptacle 296 is between the inner sidewall 30 and the outer tube surface 94 of the center tube 18. The inner receptacle 298 is defined by the inner tube surface 96 of the center tube 18. The inner receptacle 298 is similar to the tube bore 98 of the center tube 18. The inner plunger shaft 84 and the inner plunger tip 82 are slidably movable within the inner receptacle 298 along the longitudinal axis A. The outer plunger shaft 54 and the outer plunger tip 52 are seated within the outer receptacle 296 along the longitudinal axis A.

As illustrated in FIG. 4, for example, the spray tip assembly 22 is mounted to the body adaptor 20 through cooperation between the threads 282 of the spray tip insert 152 and the internal threads 112 of the body adaptor 20. The male luer lock fitting 114 is seated within the inner receptacle 278 of the spray tip insert 152 to further secure the spray tip assembly 22 to the body adaptor 20. The male luer lock fitting 114 does not extend all the way to the second end 104, and thus a clearance 294 is defined between the male luer lock fitting 114 and a portion of the first surface 254 that is located within the insert receptacle 278.

Figures 23, 24:
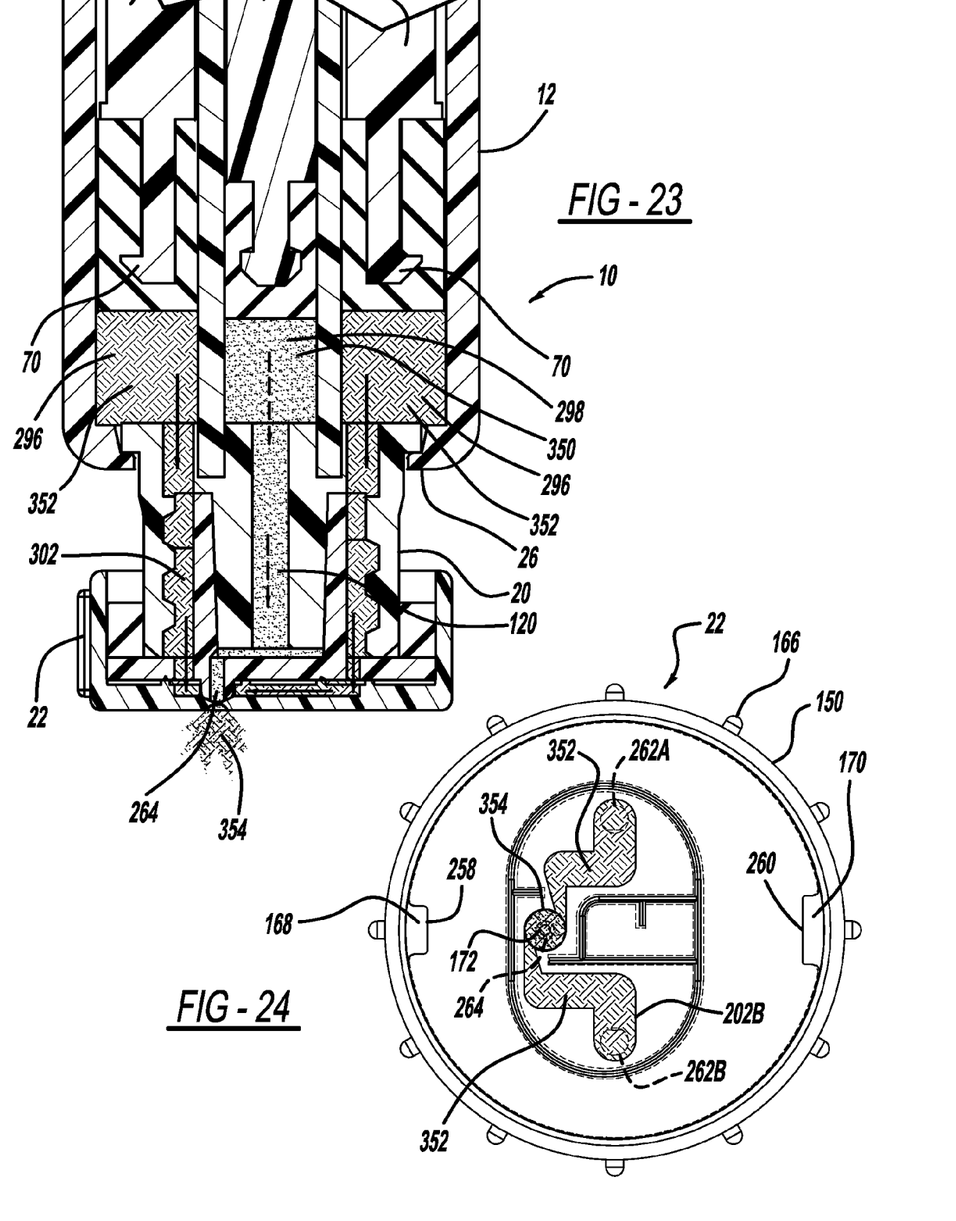
FIG. 23 is a cross-sectional view of operation of the coaxial syringe spray assembly to mix and spray a first component and a second component of a mixture.
FIG. 24 is a top view of the spray tip housing with detail of the spray tip insert overlaid thereon, and illustrating flow of the first component and the second component through the spray tip assembly.

With particularity to FIGS. 4, 23, and 24 for example, the center bore 120 of the body adaptor 20 is in fluid cooperation with the inner receptacle 298. Thus, actuation of the inner plunger 16 along the longitudinal axis A towards the second outer body end 26 of the outer body 12 will expel material, such as a suitable blood clotting serum 350 for example, out from within the inner receptacle 298 through the center bore 120 of the body adaptor 20 and into the clearance 294. From the clearance 294, the clotting serum 350 will pass through the center aperture 264 and into the first cylindrical diameter portion 174 of the outlet port 172, where the clotting serum 350 from the inner receptacle 298 is mixed with material from the outer receptacle 296, such as blood 352 to provide a clot including mixture 354.

Actuation of the outer plunger 14 along the longitudinal axis A towards the second outer body end 26 of the outer body 12 will expel material, such as the blood 352, out from within the outer receptacle 296 through each of the four body apertures 124A-D and into a collection area 302 of the spray tip assembly 22 between the insert stem 252 and the inner wall 110 of the body adaptor 20. The first recess 284 and the second recess 286 of the stem flange 280 facilitates passage of the blood 352 past the stem flange 280. From the collection area 302 the blood 352 from the outer receptacle 296 passes through the first outer aperture 262A and the second outer aperture 262B of the insert base 250 and into each of the first fluid chamber 202A and the second fluid chamber 202B. The blood 352 from the outer receptacle 296 travels to the first cylindrical diameter portion 174 of the outlet port 172 where it mixed with the clotting serum 350 from the inner receptacle 298. Due to the opposing arrangements of the first portion 204A and the first portion 204B of the first fluid chamber 202A and the second fluid chamber 202B respectively, the blood 352 from the outer receptacle 296 swirls around in the outlet port 172 about the boss 266 seated therein to provide a vortex and nearly instantaneously mix with the clotting serum 350 from the inner receptacle 298 to form a clot inducing mixture 354 having a helical flow pattern. This nearly instantaneous mixing is advantageous when mixing blood 352 and a clotting serum 350 because the clotting serum 350 will nearly instantaneously cause platelets of the blood 352 to be activated to induce wound healing.

The clot inducing mixture 354 then passes out of the outlet port 172 through the tapered portion 176 and the second cylindrical diameter portion 174, which concentrates and increases the pressure of the mixture 354, and through the conical portion 180 which causes the mixture 354 to be expelled as a mist. The mixture 354 can be applied to any suitable would site to induce clotting and healing. While the coaxial syringe spray assembly 10 is described herein as being used to mix clotting serum 350 and blood 352, any suitable materials desired to be mixed can be inserted into the outer receptacle 296 and the inner receptacle 298 and be mixed as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A coaxial syringe spray assembly comprising:

a first receptacle defined by the assembly;

a second receptacle defined by the assembly, the second receptacle is in coaxial alignment with the first receptacle; and a spray tip assembly configured to be in fluid communication with both the first receptacle and the second receptacle, the spray tip defining:

a first fluid chamber in fluid communication with the first receptacle;

a second fluid chamber in fluid communication with the first receptacle; and an outlet port that defines a blending chamber that is in fluid communication with the second receptacle, the first fluid chamber, and the second fluid chamber such that a first fluid introduced into the first fluid chamber and a second fluid introduced into the second fluid chamber are mixed in the blending chamber to provide a mixture having a helical flow pattern, wherein the outlet port provides the mixture with an outlet to exit the spray tip.

2. The coaxial syringe spray assembly of claim 1, wherein the second receptacle extends along a longitudinal axis of the assembly and the first receptacle surrounds the second receptacle.

3. The coaxial syringe spray assembly of claim 1, wherein the second receptacle is defined by an inner tube surface of a center tube mounted within an outer body of the coaxial syringe spray assembly; and wherein the first receptacle is defined between an inner sidewall of the outer body and an outer tube surface of the center tube, the center tube aligned along a longitudinal axis of the coaxial syringe spray assembly.

4. The coaxial syringe spray assembly of claim 1, wherein the spray tip assembly includes a housing and an insert mounted within the housing; and wherein the first fluid chamber, the second fluid chamber, and the blending chamber are defined in a first surface of the housing that opposes the insert.

5. The coaxial syringe spray assembly of claim 4, wherein the housing includes a second surface that is opposite to the first surface; and wherein the outlet port includes a conical portion at the second surface, the conical portion configured to provide the mixture as a spray upon exiting the outlet port.

6. The coaxial syringe spray assembly of claim 1, wherein the blending chamber is between the first fluid chamber and the second fluid chamber.

7. The coaxial syringe spray assembly of claim 1, further comprising a first plunger seated within the first receptacle and a second plunger seated within the second receptacle.

8. The coaxial syringe spray assembly of claim 3, wherein the outer body includes a body adaptor having a first end and a second end that is opposite to the first end, the inner tube is mounted to the first end and the spray tip assembly is mounted to the second end.

9. The coaxial syringe spray assembly of claim 8, wherein the body adaptor includes a center bore in fluid communication with both the second receptacle and the blending chamber; and wherein the body adaptor includes a plurality of apertures spaced apart about the center bore, the apertures provide fluid communication between the first receptacle and each of the first fluid chamber and the second fluid chamber.

10. A coaxial syringe spray assembly comprising:

a first receptacle defined by the assembly and configured to contain a first fluid;

a second receptacle defined by the assembly, the second receptacle is in coaxial alignment with the first receptacle and configured to contain a second fluid;

a spray tip assembly configured to be in fluid communication with the first receptacle and the second receptacle, the spray tip assembly defining:

a blending chamber that is in fluid communication with both the first receptacle and the second receptacle;

a first fluid chamber that is in fluid communication with the first receptacle and connected to a first portion of the blending chamber;

a second fluid chamber that is in fluid communication with the first receptacle and connected to a second portion of the blending chamber that is opposite to the first portion of the blending chamber such that the first fluid entering the blending chamber from the first fluid chamber travels in a direction opposite to the first fluid entering the blending chamber from the second fluid chamber, the first and the second fluids are mixed in the blending chamber to provide a mixture having a helical flow pattern; and an outlet port that defines the blending chamber, the outlet port includes an outlet for the mixture to exit the spray tip.

11. The coaxial syringe spray assembly of claim 10, wherein each of the first fluid chamber and the second fluid chamber are most narrow at the blending chamber.

12. The coaxial syringe spray assembly of claim 10, wherein each of the first fluid chamber and the second fluid chamber include a first portion that extends from the blending chamber, a second portion that extends at about a right angle to the first portion, and a third portion that extends at about a right angle to the second portion.

13. The coaxial syringe spray assembly of claim 12, wherein the spray tip assembly includes an insert that directs the first fluid from the first receptacle to the third portion of each of the first fluid chamber and the second fluid chamber.

14. The coaxial syringe spray assembly of claim 10, wherein the spray tip assembly includes a boss defining a center aperture in fluid communication with the second receptacle, the boss is seated within the blending chamber such that the first fluid entering the blending chamber from the first fluid chamber and the first fluid entering the blending chamber from the second fluid chamber at least initially travel about the boss in opposite directions.

15. A coaxial syringe spray assembly configured to mix blood and clotting serum, the assembly comprising:
 a first receptacle defined by the assembly and configured to contain the blood therein;
 a second receptacle defined by the assembly, the second receptacle is in coaxial alignment with the first receptacle and surrounded by the first receptacle, the second receptacle is configured to contain the clotting serum therein;
 a spray tip assembly configured to be in fluid communication with the first receptacle and the second receptacle, the spray tip assembly including:
  a blending chamber;
  a first conduit configured to convey the clotting serum from the second receptacle to the blending chamber, the first conduit partially defined by a boss that extends within the blending chamber;
  a second conduit configured to convey the blood from the first receptacle to a first portion of the blending chamber;
  a third conduit configured to convey the blood from the first receptacle to a second portion of the blending chamber that is opposite to the first portion such that blood from the first conduit and blood from the second conduit flow into the blending chamber in opposite directions, the blood flows around an exterior of the boss; and
  an outlet port;
 wherein the clotting serum and the blood are mixed in the blending chamber to provide a clotting mixture having a helical flow pattern upon exiting the spray tip at the outlet port.

16. The coaxial syringe spray assembly of claim 15, wherein the first conduit includes a center bore defined by a male luer lock.

17. The coaxial syringe spray assembly of claim 15, wherein the second conduit includes a first fluid chamber on a first side of the blending chamber and a second fluid chamber on a second side of the blending chamber that is opposite to the first side; and
 wherein the first fluid chamber is most narrow at the blending chamber and the second fluid chamber is most narrow at the blending chamber.

18. The coaxial syringe spray assembly of claim 15, wherein each of the first fluid chamber and the second fluid chamber include a first chamber portion directly connected to the blending chamber, a second chamber portion extending from the first chamber portion at about a right angle, and a third chamber portion extending from the second chamber portion at about a right angle.

19. The coaxial syringe spray assembly of claim 15, wherein platelets of the blood are activated by the clotting serum as the mixture exits the outlet port.

20. The coaxial syringe spray assembly of claim 15, further comprising a first plunger in the first receptacle and a second plunger in the second receptacle.

\* \* \* \* \*